United States Patent [19]
Back et al.

[11] Patent Number: 6,063,731
[45] Date of Patent: May 16, 2000

[54] BRASSINOSTEROID ANALOGS USEFUL AS PLANT GROWTH REGULATORS

[75] Inventors: Thomas G. Back, Calgary; Richard P. Pharis, Cochrane; Suanne K. Nakajima, Calgary, all of Canada

[73] Assignee: Agritope, Inc., Portland, Oreg.

[21] Appl. No.: 09/281,716

[22] Filed: Mar. 30, 1999

[51] Int. Cl.[7] .......................... A01N 43/36; A01N 43/02; A01N 35/00; C07J 9/00; C07D 307/89
[52] U.S. Cl. .......................... 504/138; 504/140; 504/291; 504/348; 552/541; 552/542; 549/268
[58] Field of Search ...................... 504/138, 140, 504/291, 348; 549/268; 552/541, 542

[56] References Cited

U.S. PATENT DOCUMENTS

| | | | |
|---|---|---|---|
| 4,346,226 | 8/1982 | Thompson et al. | 549/268 |
| 4,767,442 | 8/1988 | Takematsu et al. | 71/88 |
| 4,961,775 | 10/1990 | Takatsuto et al. | 71/88 |
| 5,763,366 | 6/1998 | Takatsuto et al. | 504/291 |
| 5,818,581 | 9/1998 | Hirakawa et al. | 504/140 |

OTHER PUBLICATIONS

Mori, K., and Takeuchi, T., "Synthesis of 25–Methyldolichosterone, 25–Methyl–2,3–diepidolichosterone, 25–Methylcastasterone and 25–Methylbrassinolide," *Liebigs Ann. Chem.* 818–818 (1988).

Takeno, K., and Pharis, R.P., "Brassinosteroid–Induced Bending of the Leaf Lamina of Dwarf Rice Seedlings: An Auxin–Mediated Phenomenon," *Plant & Cell Physiol.* 23(7):1275–1281 (1982).

*Primary Examiner*—Jose' G. Dees
*Assistant Examiner*—Alton Pryor
*Attorney, Agent, or Firm*—LeeAnn Gorthey; Dehlinger & Associates

[57] ABSTRACT

Disclosed are compositions and methods for promoting plant growth. The compounds are cyclopropyl- and cyclobutyl-substituted brassinosteroids having high growth promoting ability. They may be used alone or in combination with other plant growth regulating agents.

23 Claims, 5 Drawing Sheets

BRASSINOSTEROID ANALOGS USEFUL AS PLANT GROWTH REGULATORS

FIELD OF THE INVENTION

The present invention relates to compositions and methods for promoting plant growth.

REFERENCES

Adam, G. et al., in *Studies in Natural Products Chemistry*; Vol. 18, Atta-ur-Rahman, Ed; Elsevier: Amsterdam, 1996; pp. 495–549.

Back, T. G. In *Studies in Natural Products Chemistry*; Vol. 16; Atta-ur-Rahman, Ed.; Elsevier: Amsterdam, 1995; pp. 321–364.

Back, T. G. et al., *Can. J. Chem.* 71:156 (1993).

Back, T. G. et al., *J. Org. Chem.* 62:1179 (1997).

Cutler, H. G., Yokota, T., Adam, G., Eds.; *Brassinosteroids: Chemistry, Bioactivity and Applications*; ACS Symposium Series 474, American Chemical Society: Washington, D.C., 1991.

Fujioka, S. and Sakurai, A., *Natural Product Reports* 14:1 (1997).

Grove, M. D. et al., *Nature* 281:216 (1979).

Hayashi, S. et al., U.S. Pat. No. 4,886,544 (Dec. 12, 1989).

Mandava, N. B. *Ann. Rev. Plant Physiol. Plant Mol. Biol.* 39:23 (1988).

Mori, K. et al., Jpn. Kokai Tokkyo Koho JP 1-135,793, Nov. 20, 1987.

Mori, K. et al., Jpn. Kokai Tokkyo Koho JP 1-168,696; Dec. 25, 1987.

Mori, K. and Takeuchi, T. *Liebigs Ann. Chem.* 815 (1988).

Takeno, K. and Pharis, R. P., *Plant and Cell Physiol.* 23:1275 (1982).

BACKGROUND OF THE INVENTION

Brassinolide (structure (1), FIG. 1) is a steroidal natural product that was first isolated in 1979 (Grove et at.). It was shown to affect the growth of some plant species at doses as low as 1 nanogram per individual plant (Grove et al.). Subsequently, other brassinosteroids have been discovered in diverse plant natural sources (Cutler et al., Adam et al., Fujioka et al.) or synthesized (Cutler et al.; Back, 1995). It has been shown that brassinolide increases cell division and cell elongation in plants (Grove et al., Cutler et al., Adam et al., Mandava) and enhances the biosynthesis of proteins (Cutler et al., Mandava), among other physiological effects. Field trials conducted with brassinolide and certain other brassinosteroids, such as 24-epibrassinolide (2) and 28-homobrassinolide (3), have shown that applications of as little as 10–100 mg per hectare result in significant improvements in the yields of crops such as wheat, rice, potatoes, barley, and others (Cutler et al., Mandava). Improved stress resistance to drought, temperature extremes and salinity has also been noted in plants treated with brassinosteroids.

Brassinolide has been generally considered to be the most active naturally-occurring brassinosteroid. One synthetic analogue, 25-homobrassinolide (4), has been reported to be "slightly more active" than brassinolide in the rice leaf lamina inclination bioassay (Mori et al., 1988) and to promote growth of mung beans (Mori et al., 1987). Other analogs for which plant growth promoting activity has been reported include the 24-epi and 28-homo analogs of brassinolide, noted above, as well as the related keto compound, castasterone (5) (Hayashi et al.). Most of these analogs are reported to be either comparable in activity or somewhat less active than the parent compound (1).

SUMMARY OF THE INVENTION

The present invention includes, in one aspect, a plant growth promoting compound having the following structure:

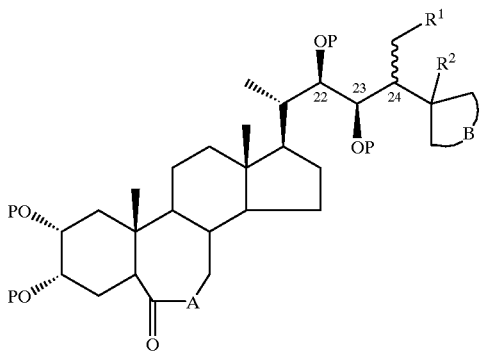

where A is oxygen or a direct bond, B is —$CH_2$— or a direct bond, OP is hydroxyl or protected hydroxyl, $R^1$ is hydrogen or methyl, and $R^2$ is hydrogen or methyl. In a preferred embodiment, the configuration at $C_{24}$ is either substantially R (α) or substantially S (β), and more preferably ubstantially S (i.e. the "natural" configuration). Other preferred embodiments include compounds in which $R^1$ is hydrogen, in which $R^2$ is hydrogen, in which A is oxygen, in which OP is hydroxyl, and compounds having these features in combination. The compounds include cyclopropyl analogs, where B is a direct bond, and cyclobutyl analogs, where B is —$CH_2$—.

In a related aspect, the invention provides a plant growth promoting composition, comprising a compound as described above, preferably where OP is hydroxyl, in a suitable delivery vehicle. The plant growth promoting composition may also include a plant growth factor, such as an auxin, a gibberellin, or a cytokinin. Preferred plant growth factors are the auxins 3-indole acetic acid (IAA) or α-naphthalene acetic acid (NAA).

In another aspect, the invention provides a method of promoting plant growth, in which an effective amount of a compound as described above, preferably where OP is hydroxyl, is applied to the plant, in a suitable delivery vehicle. The method is particularly applicable to promoting growth in cereal crops. The compound may be applied in combination with a plant growth factor as described above. Preferably, the combination is such that its application promotes growth to a greater extent than a combination of the effects produced by the compound and the plant growth factor when each is administered separately.

These and other objects and features of the invention will become more fully apparent when the following detailed description of the invention is read in conjunction with the accompanying drawings.

DETAILED DESCRIPTION OF THE INVENTION

I. Brassinolide Analogs

The plant growth promoting compounds of the invention have the following general structure:

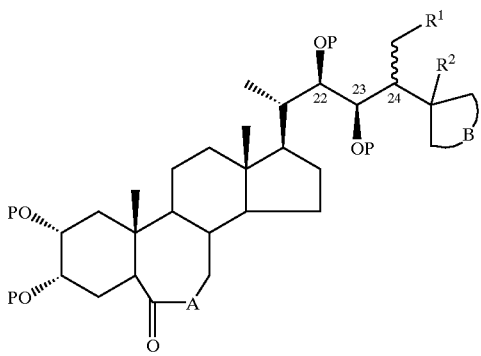

where

A is oxygen or a direct bond,

B is —$CH_2$— or a direct bond,

OP is hydroxyl or protected hydroxyl, $R^1$ is hydrogen or methyl, and $R^2$ is hydrogen or methyl.

These compounds, having the absolute configuration shown, are cyclopropyl- and cyclobutyl-substituted analogs of brassinolide (where B is a direct bond or —$CH_2$—, respectively), shown to have high biological activity, as demonstrated below. In certain embodiments, the structure of the compounds otherwise corresponds to the 'natural' structure; i.e. where $R^1$ and $R^2$ are hydrogen, $C_{24}$ has the S (β) configuration, and A is oxygen. However, the compounds may also include other variations from the 'natural' structure, particularly those which are known to produce plant growth promoting compounds. These include the 24-epi compound (where $C_{24}$ has the R configuration), the 28-homo compound (where $R^1$ is methyl), the 25-homo compound (where $R^2$ is methyl), and the keto analog (where A is a direct bond). The keto analog is also a direct synthetic precursor to the lactone compound.

The invention compounds also include those in which the hydroxyl and/or carbonyl groups are protected with removable protecting groups, such as hydrolyzable esters, ketals or acetals. As used herein, "protected hydroxyl" refers to a group which is readily converted to hydroxyl, for example, a hydrolyzable ester, a lower alkyl (i.e. $C_1$ to $C_6$), benzyl, trityl, allyl, or alkylsilyl ether, or an acetal (alkoxyalkyl ether). Since the hydroxyl groups of the subject compounds form cis-diols, cyclic acetals or ketals, e.g. acetonides, may also be used as protecting groups. Cyclic ketals, formed by the addition of a cis-diol, are also commonly used as carbonyl protecting groups. Such protecting groups are widely used in organic synthesis and in preparation of prodrugs and are well known in the art.

III. Synthesis

Figure 1:
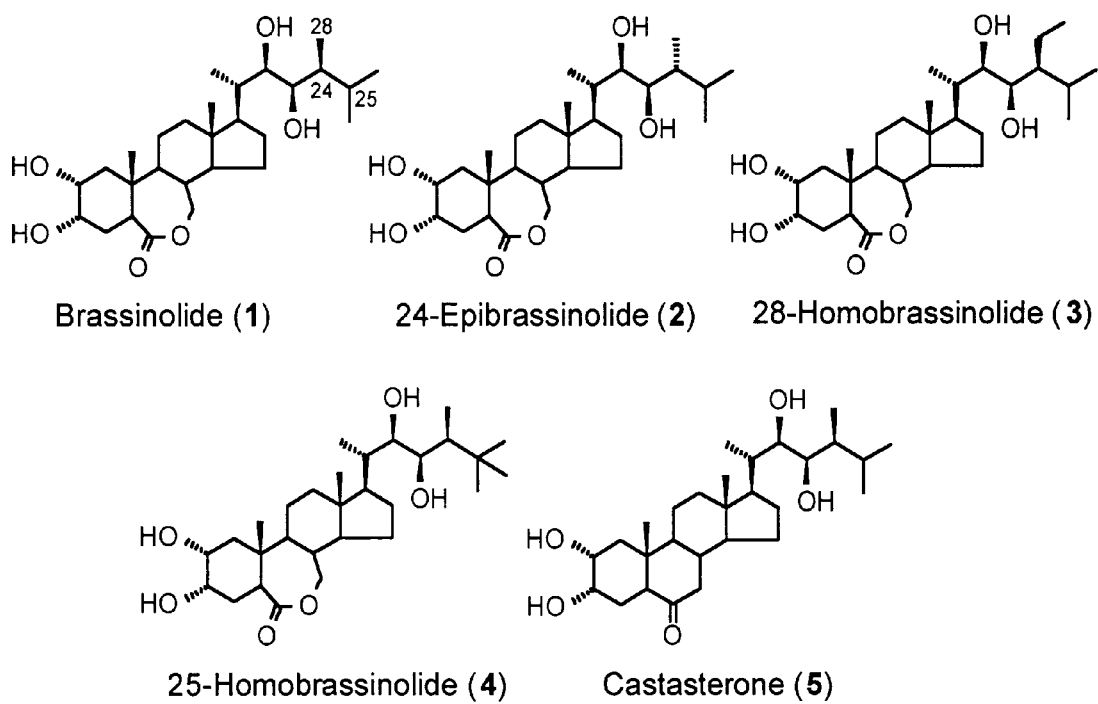
FIG. 1 shows representative members of the brassinosteroid family.
Figure 2A:
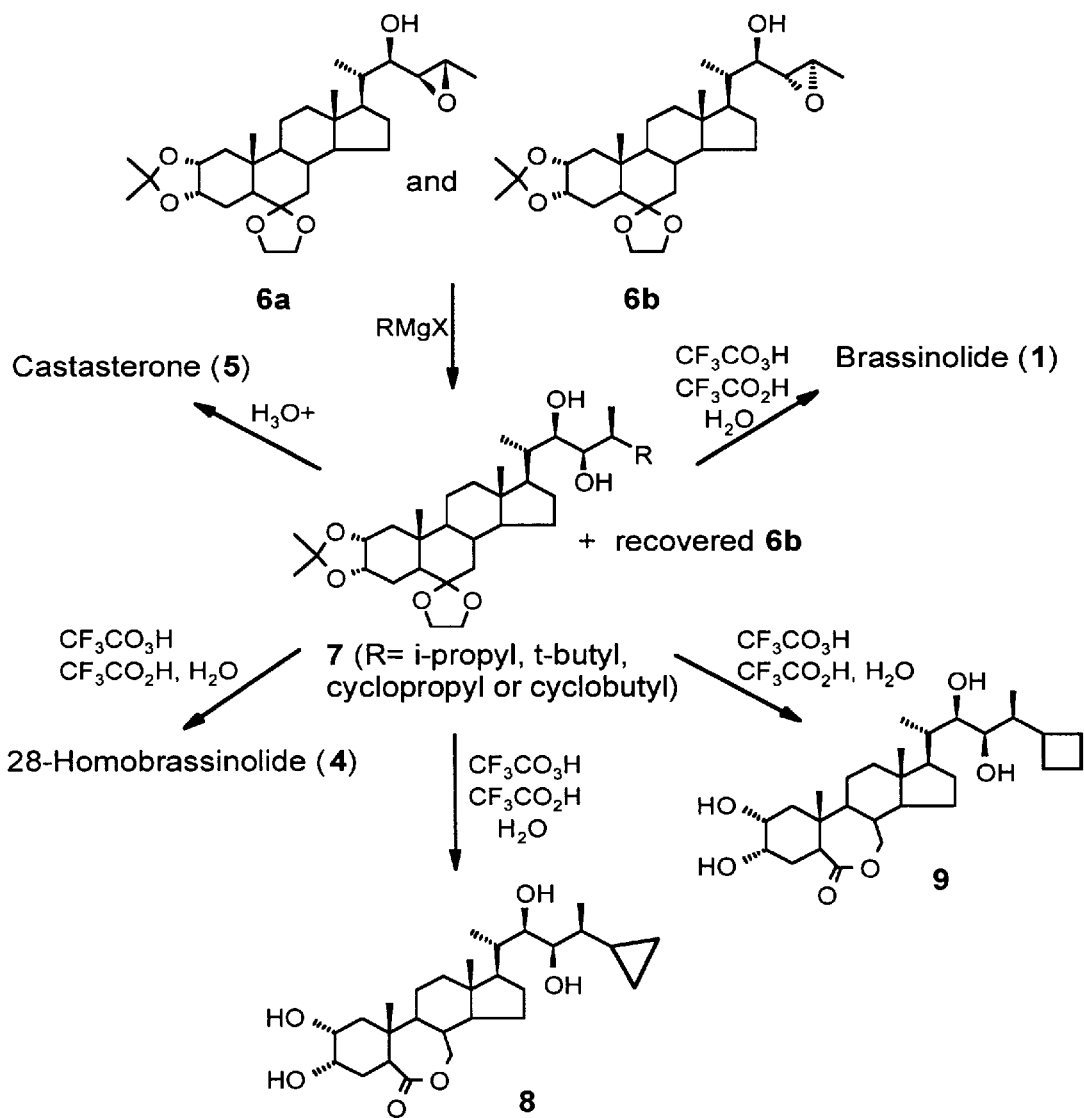
FIGS. 2A–2B show methods of preparing compounds of the invention.

Brassinolide (1) and the related brassinosteroid castasterone (5) may be prepared by ring-opening of threo-epoxide 6a with isopropylmagnesium chloride (isopropyl Grignard reagent), followed by simultaneous deprotection and Baeyer-Villiger oxidation, or acid-catalyzed hydrolysis, respectively, of intermediate 7 (R=isopropyl; FIG. 2A), according to the procedure of Back et al. The erythroepoxide 6b reacts more slowly than 6a and is recovered unreacted. This method permits the introduction of different side chains at C-24 by choice of the appropriate Grignard reagent at a late (penultimate) step of the synthesis.

The invention compounds 8 and 9 were thus prepared from epoxide 6a via 7 (R=cyclopropyl and cyclobutyl, respectively; FIG. 2A). Detailed procedures for the preparation of 8 and 9 are given in the Examples, below. The 25-homo analogs of these compounds may be prepared by use of the corresponding methylcyclopropyl and methylcyclobutyl Grignard reagents. The known 25-homo analog of brassinolide (4) was prepared by this method, using the t-butyl Grignard reagent, for the purpose of comparison with parent compound 1 and with present compounds 8 and 9.

The corresponding 28-homo compounds may be prepared from the 28-homo analog of the epoxide 6a, i.e. the corresponding ethyl-substituted epoxide. This structure, in turn, may be prepared by a modification of the preparation described in Back et al. for epoxide 6a; e.g. by using n-propyl iodide rather than ethyl iodide in preparing the alkylselenium reagent which is added to the aldehyde precursor.

Figure 2B:
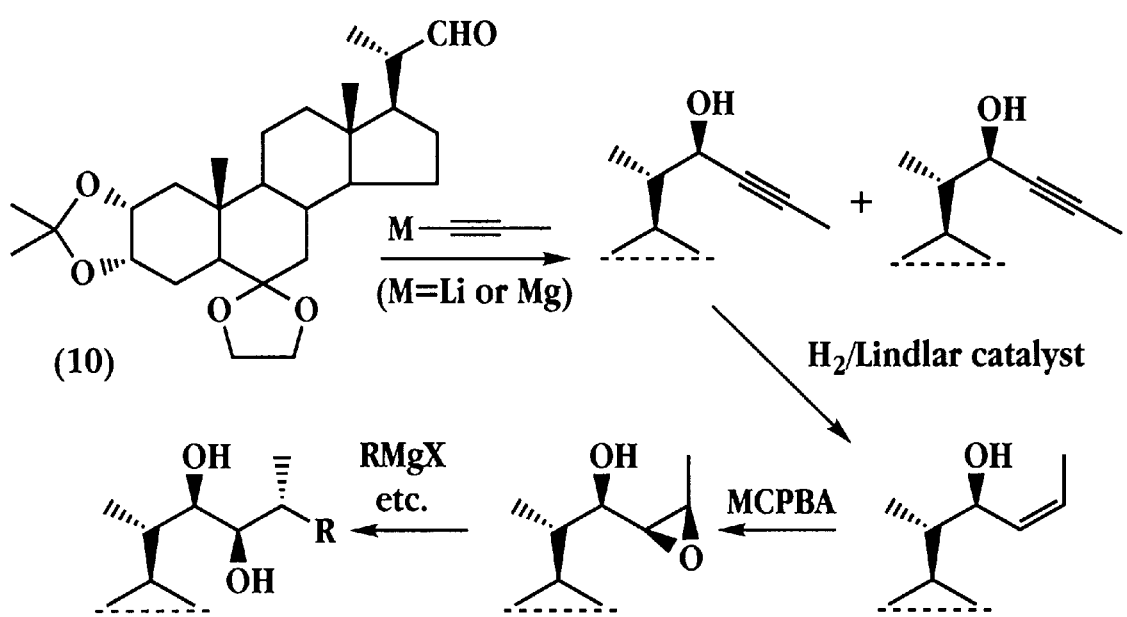

The 24-epi analogs may be prepared, as shown in FIG. 2B, by adding the acetylide anion of propyne to the aldehyde 10 (see Back et al.), followed by partial hydrogenation to the olefin and epoxidation with, e.g., a peracid such as m-chloroperoxybenzoic (MCPBA). The epoxide intermediate shown is the major expected stereoisomer. This epoxide is then reacted with a cyclopropyl or cyclobutyl Grignard reagent, as shown in FIG. 2A.

III. Biological Activity

A. Rice Leaf Lamina Inclination Assay

Several methods have been devised for measuring the bioactivity of brassinosteroids (Cutler et al., Adam et al., Mandava). Of these, the rice leaf lamina inclination assay (Takeno et al.) has come to be widely used and accepted because it provides a rapid, highly sensitive (detection limits of 1 are <1 ng/plant) and reproducible protocol.

Figure 3:
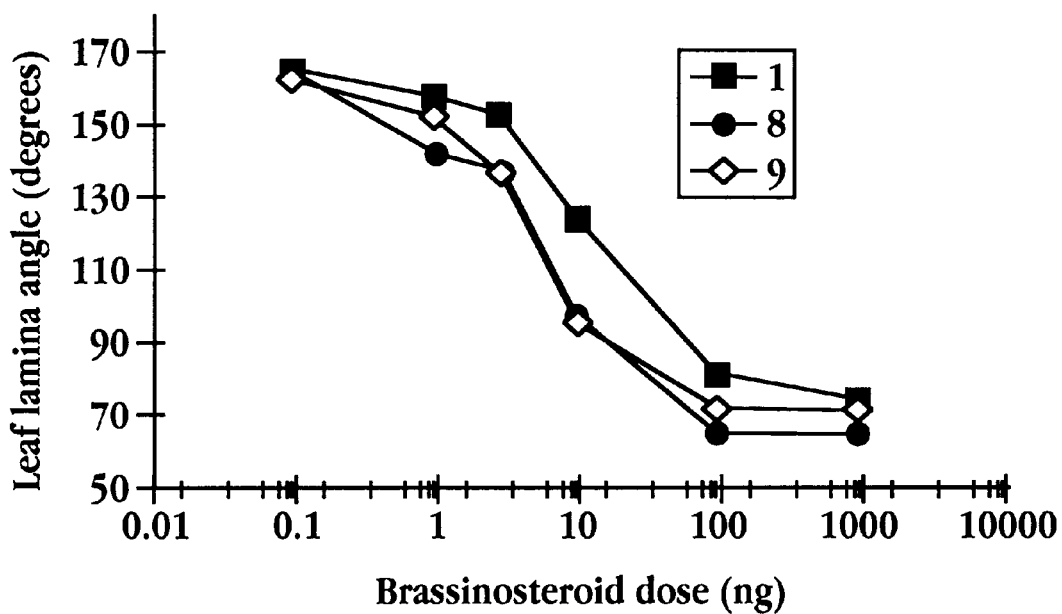
FIG. 3 shows the effect of brassinolide (1) and invention compounds 8 and 9 on leaf lamina angle in the rice leaf lamina assay.

Compounds 8 and 9 were tested in the rice leaf lamina inclination bioassay against brassinolide (1) as a standard. The results are shown in FIG. 3, where the leaf lamina angle is plotted against the dose per plant in nanograms on a logarithmic scale. FIG. 3 shows that both 8 and 9 are about five times as active as brassinolide; that is, it requires about five times the dose of brassinolide to obtain the same lamina angle as with a given dose of 8 and 9.

Figure 4:
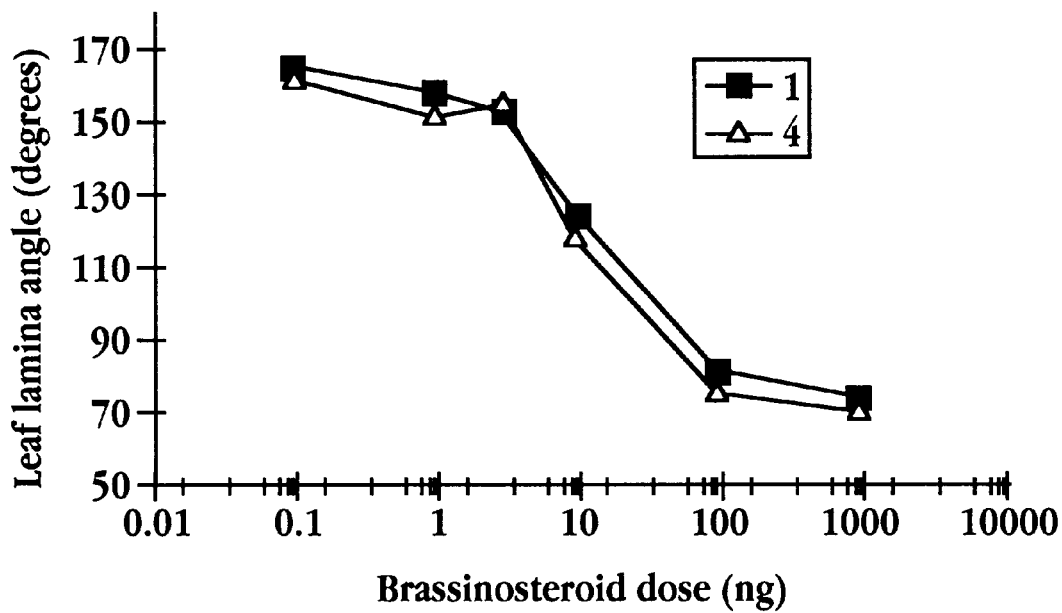
FIG. 4 shows the effect of brassinolide (1) and the known 28-homo analog (4) on leaf lamina angle in the rice leaf lamina assay.

The activity of the 25-homo analog 4 vs. 1 in the rice leaf lamina inclination bioassay is shown for comparison in FIG. 4. The activity of 4 is very similar to that of parent compound 1 at all dosage levels. Thus, both present compounds 8 and 9 show higher activity than either 1 or 4 across a wide range of dosage levels.

Figure 5:
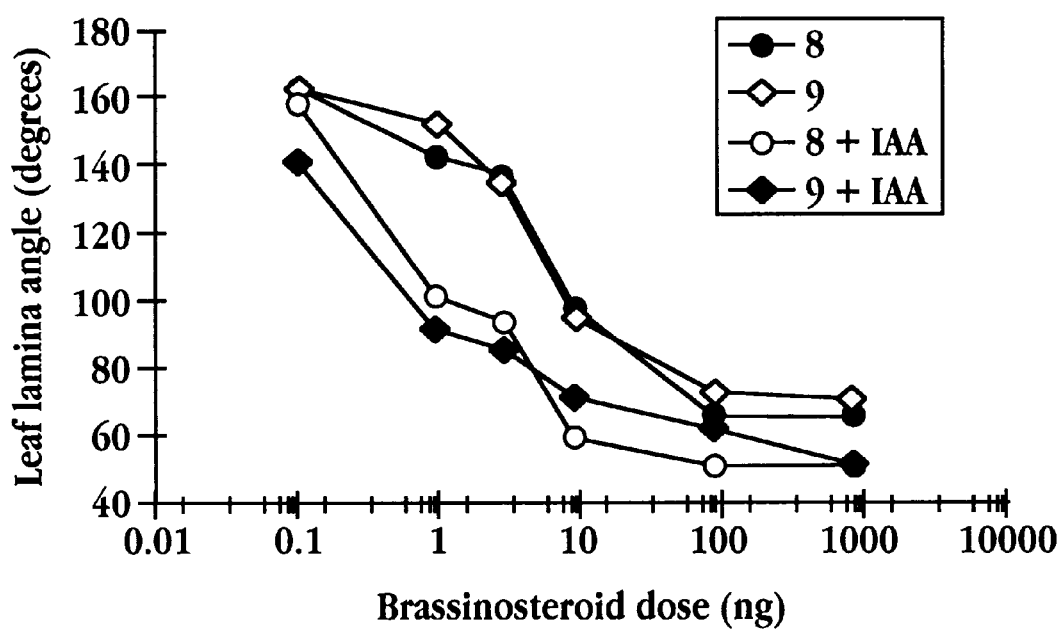
FIG. 5 shows the effect of invention compounds 8 and 9, alone and in combination with IAA (3-indoleacetic acid), on leaf lamina angle in the rice leaf lamina assay.

Compounds 8 and 9 also exhibit strong synergy with the auxin IAA (3-indoleacetic acid) (FIG. 5). The bioassays were carried out using dwarf rice *Oryza sativa* var. Tanginbozu, as described by Takeno and Pharis. The brassinosteroids were dissolved in 95% ethanol and applied as 0.5 μl microdrops to the rice plant, at 0.1 to 1000 ng/plant, 48 h after planting germinated seeds on 0.8% water agar. For combination treatments, 1000 ng of IAA was similarly applied per plant about 2 h prior to the application of the brassinosteroids. The leaf lamina angle was measured 60–65 h after brassinosteroid application. Each data point is the mean of the leaf angles from about 36 plants for doses up to 100 ng, and from about 24 plants for the 1000 ng doses.

Parallel applications of ethanol alone, IAA (1000 ng) in ethanol, 1 alone and 1 plus IAA were also carried out as controls. Ethanol alone and IAA in ethanol gave leaf lamina angles of 163° and 164°, respectively, showing that IAA alone had no discernable effect.

The results obtained by the simultaneous addition of 1000 nanograms of the auxin together with the indicated brassinosteroid doses are shown in FIG. 5. Roughly a ten-fold increase in activity was observed at most dosage levels when the auxin was included.

"Auxin" is a general name for a group of hormones involved with growth responses in plants. They are believed to have the effect of making the plant cell wall less rigid and allowing elongation. Naturally occurring auxins include IAA, used above, as well as indole ethanol, indole acetaldehyde, indole acetonitrile, phenylacetic acid, 4-chloroindoleacetic acid, and indolebutyric acid. The first three are probably converted to IAA in vivo. Synthetic auxins (i.e., synthetic compounds that show auxin activity) include a-naphthalene acetic acid (NAA, used below), 2,4-dichlorophenoxyacetic acid, and 2,4,5-trichlorophenoxyacetic acid.

The compounds of the invention may also be used in combination with other plant growth factors. Major classes are the cytokinins and the gibberellins. Cytokinins are derived from the purine adenine and are active in promoting cell division; they are also involved in cell growth and differentiation and in other physiological processes. Naturally occurring cytokinins include zeatin and its riboside and benzyl adenine. Other cytokinins commonly used in plant tissue culture include kinetin and 2-isopentyladenine. Gibberellins are diterpenoid compounds related to gibberellic acid ($GA_3$) and are involved in promotion of stem elongation, mobilization of food reserves in seeds, and other plant growth processes. Many endogenous gibberellins have been found in plants, and others have been prepared synthetically from gibberellic acid, which can be obtained from the growth medium of the fungus *Gibberella fujikuroi*.

B. Growth Promotion in Wheat

A field trial to compare the effects of brassinode (1) and the cyclopropyl analog 8, with and without and added auxin (α-naphthalene acetic acid, NAA) on wheat was carried out at the Agriculture Canada research station in Lacombe, Alberta. The results are shown in Table 1. As shown in the Table, treatment with 8 produced about a 6% greater yield than treatment with the parent compound 1. Spraying with a solution containing 10 μg/liter of 8 and 20 mg/liter of NAA gave a significantly higher yield (684 grams per square meter) than obtained with either 1 a mixture of 1 and NAA.

TABLE 1

Effect of 1 or 8 with and without NAA on Wheat Yield

| NAA (mg/L) | 1 (μg/L) | 8 (μg/L) | Yield (g/m²) |
| --- | --- | --- | --- |
| 0 | 0 | 0 | 595 |
| 20 | 0 | 0 | 647 |
| 0 | 10 | 0 | 546 |
| 0 | 0 | 10 | 577 |
| 20 | 10 | 0 | 573 |
| 20 | 0 | 10 | 684 |

The brassinolde analogs 8 and 9, having cyclopropyl- and cyclobutyl-substituted side chains, show exceptionaly high biological activities, exceeding that of both brassinolide (1) and 25-homobrassinolde (4), the most potent previously known brassinosteroids. These analogs can thus be employed at lower doses, making their applications less expensive. The compounds can also be used to great advantage in combination with a less expensive plant growth factor, e.g. an auxin, as shown above, a gibberellin, or a cytokinin, thus further reducing required doses and cost. Other applications of the brassinosteroids 8 and 9 include their use in the activation of brassinosteriod-responsive genes in transgenic plants.

IV. Formulations and Methods of Application

The compounds of the invention may be used either alone or in combination. They may be applied in combination with adjuvants such as spreading agents, wetting agents, dispersants, or binding agents, or admixed with agricultural additives such as insecticides, fungicides, herbicides, soil disenfectants, or fertilizers. The dosage form may be, for example, a liquid, suspension, emulsion, powder, wettable powder, granules, or tablets.

A preferred liquid vehicle is an aqueous solvent. Other liquid carriers that may be used include alcohols such as methanol, butanol and glycol, ketones such as acetone, hydrocarbons such as toluene, xylene and cyclohexane, amides such as dimethylformamide, sulfoxides such as dimehtylsulfoxide, animal and vegetable oils, and fatty acids and their esters. A surfactant may be employed as an emulsifier or dispersing agent. Nonionic or anionic surfactants, such as polyethylene oxide derivatives, fatty acid esters, sodium alkyl sulfates, and quaternary ammonium salts, are commonly employed.

Solid carriers that may be used include, for example, clay, talc, diatomaceous earth, silica, calcium carbonate, bentonite, quartz, alumina, vermiculite, vegetable-based organic materials such as soybean powder, wheat flour, wood flour, starch and crystalline cellulose; polymeric substances such as alkyd resin, polyalkyleneglycol, ketone resin, ester gum, copal gum and dammar gum; and waxes such as carnauba wax and beeswax.

Such formulations are prepared by means of standard procedures of agrochemical manufacture. The concentration of the active ingredient(s) in the formulation varies with the crop plant, type of formulation, method of application, treating time and period, and other conditions. When applied as a solution or dispersion in water or an organic solvent, a concentration of $10^{-5}$ ppm to 10 ppm, and more preferably $10^{-3}$ ppm to 0.1 ppm of active ingredient, is preferable. The compounds of the invention are effective in very small amounts per plant. The amount applied is generally between 1 picogram to 100 μg per plant, preferably about 0.1 to 10 μg per plant, or 100 μg to 1 g per acre, preferably about 0.5 to 100 mg per acre.

The appropriate treating area, treating method, and treating time or season are determined in accordance with standards known in the field. Effective methods of administration include immersion, prior to planting, of seedings, plantings or root plants, spraying of plant surfaces during the growth period, injection into plants, or application onto the soil. The application can be repeated as needed. For increasing the yield of cereal crops, the compounds are preferably applied at about the time of flowering; i.e., the period from the beginning of formation of reproductive cells to nearly the end of seed or fruit ripening.

Beneficial effects of plant growth regulators, such as those described herein, include growth promotion, enhanced crop quality, and increased resistance to disease, herbicides, bactericides, insecticides, low temperature or high temperature stress, and moisture stress. Crops whose growth may be regulated include graminaceous crops (i.e. cereals) such as rice, wheat, corn, barley, or oats, fruit trees, beans, such as soy beans, coffee or cocoa, root crops, fruity vegetables, leafy vegetables, woody plants, and flowering plants.

While the invention has been described with reference to specific methods and embodiments, it will be appreciated that various modifications may be made without departing from the invention.

EXAMPLES

Preparation of Cyclopropyl Analog 8

Cyclopropylmagnesium bromide (10.25 mmol) in 20 mL of THF was added to a suspension of CuCN (51 mg, 0.57 mmol) in 10 mL of THF at −78° C. and stirred for 1 h. A mixture of epoxides 6a and 6b (575 mg, 1.14 mmol, in the ratio of 1.2:1) in 10 mL of THF was then added dropwise, and stirring was continued for 1 h at −78° C. and 4 h at 0° C. The reaction was quenched with 20% $NH_4Cl$ solution and the mixture was extracted three times with ether. The organic layers were combined, washed with $NaHCO_3$ solution and brine, and dried over anhydrous $MgSO_4$. The solvent was evaporated and flash chromatography of the residue (elution with 30–60% ether-hexanes) afforded 90% of recovered erythro-epoxy alcohol 6b and 76% (based on threo-epoxide 6a) of the corresponding 7 (R=cyclopropyl) as a colorless oil: IR 3478, 1456, 1378, 1229, 1055 $cm^{-1}$; $^1$H-NMR (200 MHz, $CDCl_3$) δ 4.29 (m, 1 H), 4.14 (m, 1 H), 3.95 (m, 3 H), 3.74 (m, 2 H), 3.58 (br d, J =7.0 Hz, 1 H), 1.48 (s, 3 H), 0.96 (d, J=6.6 Hz, 3 H), 0.88 (d, J=6.4 Hz, 3 H), 0.84 (s, 3 H), 0.66 (s, 3 H, 0.49 (br t, J=7.0 Hz, 2 H), 0.13 (br d, J=4.9 Hz, 2 H); $^{13}$C-NMR (100 MHz, $CDCl_3$) δ 109.7 (C), 107.5 (C), 76.1 (CH), 73.9 (CH), 72.9 (CH), 72.8 (CH), 65.4 ($CH_2$), 64.1 ($CH_2$), 55.8 (CH), 52.9 (CH), 52.3 (CH), 45.4 (CH), 42.6 ($CH_2$), 42.3 (C), 40.9 ($CH_2$), 40.3 (CH), 39.7 ($CH_2$), 37.9 (C), 37.1 (CH), 32.9 (CH), 28.5 ($CH_3$), 27.7 ($CH_2$), 26.5 ($CH_3$), 24.0 ($CH_2$), 21.9 ($CH_2$), 20.7 ($CH_2$), 15.7 (CH), 13.3 ($CH_3$), 12.5 ($CH_3$), 11.9 ($CH_3$), 11.8 ($CH_3$), 4.3 ($CH_2$), 4.0($CH_2$); mass spectrum, m/z (relative intensity %) 546 ($M^+$, 2), 531 ($M^+$-$CH_3$, 4), 446 (9), 431 (46), 235 (100). Exact mass calculated for $C_{33}H_{54}O_6$: 546.3920. Found: 546.3904.

Aqueous 30% hydrogen peroxide (0.34 mL) was added to 2.82 mL of trifluoroacetic anhydride at 0° C. and the mixture was stirred for 30 min. In a separate vessel, trifluoroacetic acid (3.0 mL) was added to 7 (R=cyclopropyl) (260 mg, 0.476 mmol) in 10 mL of chloroform and stirring was continued for 40 min. The latter solution was then added dropwise to the pregenerated trifluoroperoxyacetic acid solution at 0° C., followed by stirring for an additional 1.5 h at room temperature. The mixture was diluted with chloroform, washed with water and 10% $Na_2SO_3$ solution, dried over anhydrous $MgSO_4$ and evaporated in vacuum. Flash chromatography of the residue (elution with 5–10% methanol-chloroform) provided 152 mg (67%) of a mixture of 8 and its 6-oxa regioisomer in a 9:1 ratio (NMR integration). Recrystallization from methanol afforded 112 mg (49%) of pure 8: mp 272–274° C.; IR 3418, 1711, 1456, 1387, 1066 $cm^{-1}$; $^1$H-NMR (200 MHz, $CDCl_3$) δ 4.08 (m, 3 H) 3.72 (m,2H), 3.57 (br d, J=9.1 Hz, 1 H), 3.13 (dd, J=6.9, 4.7 Hz, 1 H), 0.97 (d, J=6.4 Hz, 3 H), 0.93 (s, 3 H), 0.89 (d, J=6.6 Hz, 3 H), 0.70 (s, 3 H), 0.54 (t, J=7.4 Hz, 2 H), 0.15 (d, J=4.6 Hz, 2 H); $^{13}$C-NMR (100 MHz, $CDCl_3$-$CD_3OD$) δ 177.2 (C), 75.8 (CH), 73.4 (CH), 70.4 ($CH_2$),67.7 (two CH), 57.9 (CH), 52.0 (CH), 51.1 (CH), 42.2 (C), 41.0 ($CH_2$), 40.8 (CH), 40.3 (CH), 39.5 ($CH_2$), 38.9 (CH), 38.0 (C), 37.0 (CH), 31.0 ($CH_2$), 27.3 ($CH_2$), 24.5 ($CH_2$), 22.0 ($CH_2$), 15.5 (CH), 15.2 ($CH_3$), 12.3 ($CH_3$), 11.6 ($CH_3$), 11.5 ($CH_3$), 4.1 ($CH_2$), 3.9 ($CH_2$); mass spectrum, m/z (relative intensity %) 478 ($M^+$, 1), 460 ($M^+$-$H_2O$, 2), 409 ($M^+$-cyclopropyl), 379 (16), 350 (42), 41 (100). Anal. calculated for $C_{28}H_{46}O_6$: C, 70.26; H, 9.69. Found: C, 70.26; H, 9.60.

Preparation of Cyclobutyl Analog 9

A mixture of epoxides 6a and 6b (400 mg, 0.793 mmol, in a 1.5:1 ratio) was treated with cyclobutylmagnesium chloride (1.59 mmol), using the same procedure as in the preparation of 8, above. Flash chromatography of the crude product (elution with 40–70% ether-hexanes) afforded 85% of recovered erythro-epoxide 6b and 78% (based on threo-epoxide 6a) of the corresponding 7 (R=cyclobutyl) as a colorless oil: IR 3439, 1454, 1375, 1228, 1051 $cm^{-1}$; $^1$H-NMR (200 MHz, $CDCl_3$) δ 4.29 (m, 1 H), 4.10 (m, 1 H), 3.95 (m, 3 H), 3.75 (m, 1 H), 3.52 (br s, 2 H), 1.50 (s, 3 H), 1.35 (s, 3 H), 0.90 (d, J=5.9 Hz, 3 H), 0.84 (s, 3 H), 0.73 (d, J=6.8 Hz, 3 H), 0.69 (s, 3 H); $^{13}$C-NMR (100 MHz, $CDCl_3$) δ 109.7 (C), 107.6 (C), 74.5 (CH), 73.0 (CH), 72.9 (CH), 72.2 (CH), 65.5 ($CH_2$), 64.2 ($CH_2$), 55.9 (CH), 52.9 (CH), 52.4 (CH), 45.5 (CH), 42.7 ($CH_2$), 42.3 (C), 41.0 (CH), 39.7 ($CH_2$), 38.9 (CH), 38.0 (C), 36.8 (CH), 33.0 (CH), 28.6 ($CH_3$), 27.7 ($CH_2$), 27.5 ($CH_2$), 27.0 ($CH_2$), 26.6 ($CH_3$), 24.0 ($CH_2$), 22.0 ($CH_2$), 20.8 ($CH_2$), 17.5 ($CH_2$), 13.4 ($CH_3$), 11.94 ($CH_3$), 11.85 ($CH_3$), 9.0 ($CH_3$); mass spectrum, m/z (relative intensity %) 560 ($M^+$, 11), 545 ($M^+$-$CH_3$, 33), 446 (18), 431 (58), 235 (100). Exact mass calculated for $C_{34}H_{56}O_6$: 560.4077. Found: 560.4101.

The above compound 7 (R=cyclobutyl) (209 mg, 0.373 mmol) was treated with trifluoroperoxyacetic acid as in the procedure for the preparation of 8. Flash chromatography (elution with 5–10% methanol-chloroform) provided 113 mg (62%) of a mixture of 9 and its 6-oxa regioisomer in a 9:1 ratio (NMR integration). Recrystallization from methanol afforded 83 mg (45%) of pure 9: mp 284–286° C.; IR 3415, 1714, 1457, 1389, 1065 $cm^{-1}$; $^1$H-NMR (400 MHz, $CDCl_3$) δ 4.12 (m, 2 H), 4.03 (m, 1 H), 3.72 (m, 1 H), 3.53 (br s, 2 H), 3.13 (dd, J=7.7, 4.5 Hz, 1 H), 0.94 (s, 3 H), 0.92 (d, J=6.6 Hz, 3 H), 0.74 (s, 3 H), 0.73 (d, J=6.8 Hz, 3 H); $^{13}$C-NMR (100 MHz, $CDCl_3$-$CD_3OD$) δ 177.2 (C), 73.8 (CH), 71.7 (CH), 70.5 ($CH_2$), 67.7 (two CH), 58.0 (CH), 52.0 (CH), 51.1 (CH), 42.2 (C), 41.03 ($CH_2$), 41.0 (CH), 40.8 (CH), 39.5 ($CH_2$), 39.0 (CH), 38.7 (CH), 38.1 (C), 36.6 (CH), 31.0 ($CH_2$), 27.33 ($CH_2$), 27.25 ($CH_2$), 26.9 ($CH_2$), 24.5 ($CH_2$), 22.1 ($CH_2$), 17.3 ($CH_2$), 15.2 ($CH_3$), 11.5 (two $CH_3$), 8.7 ($CH_3$); mass spectrum, m/z (relative intensity %) 406 (1), 380 (10), 361 (23), 107 (67), 81 (100). Anal. calculated for $C_{29}H_{48}O_6$: C, 70.70; H, 9.82. Found: C, 70.88; H, 10.03.

It is claimed:

1. A plant growth promoting compound having the structure:

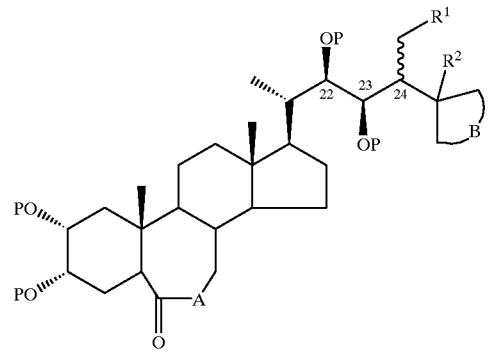

where

A is oxygen or a direct bond,

B is —$CH_2$— or a direct bond,

OP is hydroxyl or protected hydroxyl, $R^1$ is hydrogen or methyl, and $R^2$ is hydrogen or methyl.

2. The compound of claim 1, where the configuration at $C_{24}$ is either substantially R ($\alpha$) or substantially S ($\beta$).

3. The compound of claim 2, where the configuration at $C_{24}$ is substantially S ($\beta$).

4. The compound of claim 1, where $R^1$ and $R^2$ are hydrogen.

5. The compound of claim 3, where $R^1$ and $R^2$ are hydrogen.

6. The compound of claim 5, where A is oxygen.

7. The compound of claim 6, where B is —$CH_2$— and OP is hydroxyl.

8. The compound of claim 6, where B is a direct bond and OP is hydroxyl.

9. A plant growth promoting composition comprising a compound having the structure of claim 1, where OP is hydroxyl, in a suitable delivery vehicle.

10. The composition of claim 9, wherein in said compound, the configuration at $C_{24}$ is substantially S, $R^1$ and $R^2$ are hydrogen, and A is oxygen.

11. The composition of claim 10, wherein in said compound, B is —$CH_2$—.

12. The composition of claim 10, wherein in said compound, B is a direct bond.

13. The composition of claim 9, further comprising a plant growth factor selected from the group consisting of an auxin, a gibberellin, and a cytokinin.

14. The composition of claim 13, wherein said plant growth factor is an auxin.

15. The composition of claim 14, wherein said plant growth factor is 3-indole acetic acid (IAA) or $\alpha$-naphthalene acetic acid (NAA).

16. A method of promoting plant growth, comprising applying to the plant, in a suitable delivery vehicle, an effective amount of a compound having the structure of claim 1, where OP is hydroxyl.

17. The method of claim 16, wherein in said compound, the configuration at $C_{24}$ is substantially S, $R^1$ and $R^2$ are hydrogen, and A is oxygen.

18. The method of claim 17, wherein in said compound, B is —$CH_2$—.

19. The method of claim 17, wherein in said compound, B is a direct bond.

20. The method of claim 16, where said plant is a cereal crop.

21. The method of claim 16, further comprising applying to said plant a plant growth factor selected from the group consisting of an auxin, a gibberellin, and a cytokinin.

22. The method of claim 21, wherein said plant growth factor is an auxin.

23. The method of claim 22, wherein said plant growth factor is 3-indole acetic acid (IAA) or $\alpha$-naphthalene acetic acid (NAA).

* * * * *